United States Patent
Castro et al.

(10) Patent No.: US 6,299,639 B1
(45) Date of Patent: Oct. 9, 2001

(54) SELF-AGGREGATING PROTEIN COMPOSITIONS AND USE AS SEALANTS

(75) Inventors: Dan Castro, Jersey City; Al Kuehn, Wayne; Moon Hae Sunwoo, Old Tappan, all of NJ (US)

(73) Assignee: Meadox Medicals, Inc., Oakland, NJ (US)

(*) Notice: Subject to any disclaimer, the term of this patent is extended or adjusted under 35 U.S.C. 154(b) by 0 days.

(21) Appl. No.: 09/292,688

(22) Filed: Apr. 15, 1999

Related U.S. Application Data

(62) Division of application No. 08/814,533, filed on Mar. 10, 1997, now Pat. No. 6,177,609.

(51) Int. Cl.[7] .................................................. A61F 2/10
(52) U.S. Cl. ........................................ 623/1.47; 623/11.11
(58) Field of Search .................................. 623/11.11, 1.1, 623/1.44, 1.45, 1.46, 1.47, 1.48; 426/657; 427/2.25; 424/422

(56) References Cited

U.S. PATENT DOCUMENTS

| | | |
|---|---|---|
| 3,425,418 | 2/1969 | Chvapil et al. . |
| 3,562,352 | 2/1971 | Nyilas . |
| 3,766,104 | 10/1973 | Bonin et al. . |
| 3,804,812 | 4/1974 | Koroscil . |
| 4,061,787 | 12/1977 | Higgins . |
| 4,097,234 | 6/1978 | Sohde et al. . |
| 4,279,812 | 7/1981 | Cioca . |
| 4,390,519 | 6/1983 | Sawyer . |
| 4,404,970 | 9/1983 | Sawyer . |
| 4,412,947 | 11/1983 | Cioca . |
| 4,440,680 | 4/1984 | Cioca . |
| 4,515,637 | 5/1985 | Cioca . |
| 4,606,910 | 8/1986 | Sawyer . |
| 4,642,117 | 2/1987 | Nguyen et al. . |
| 4,695,280 | 9/1987 | Watanabe et al. . |
| 4,738,849 | 4/1988 | Sawyer . |
| 4,755,593 | 7/1988 | Lauren . |
| 4,784,659 | 11/1988 | Fleckenstein et al. . |
| 4,837,285 | 6/1989 | Berg et al. . |
| 4,842,575 | 6/1989 | Hoffmann, Jr. et al. . |
| 4,902,290 | 2/1990 | Fleckenstein et al. . |
| 4,969,912 | 11/1990 | Kelman et al. . |
| 5,100,783 | 3/1992 | Dean, Jr. et al. . |
| 5,108,424 | 4/1992 | Hoffmann, Jr. et al. . |
| 5,157,111 | 10/1992 | Pachence . |
| 5,197,977 | 3/1993 | Hoffmann, Jr. et al. . |
| 5,256,140 | 10/1993 | Fallick . |
| 5,290,271 | 3/1994 | Jernberg . |
| 5,318,524 | 6/1994 | Morse et al. . |
| 5,332,803 | 7/1994 | Kelman et al. . |
| 5,336,616 | 8/1994 | Livesey et al. . |
| 5,565,318 | 10/1996 | Walker et al. . |

FOREIGN PATENT DOCUMENTS

| | | |
|---|---|---|
| 0 585 476 | 3/1994 | (EP) . |
| 0 698 395 | 2/1996 | (EP) . |
| 0 698 396 | 2/1996 | (EP) . |
| 2 187 463 | 9/1987 | (GB) . |
| 994275 | 6/1965 | (HU) . |
| WO 83/03536 | 10/1983 | (WO) . |
| 93-173464 | 4/1989 | (WO) . |

OTHER PUBLICATIONS

Collagen Coatings as Biological Sealants For Textile Arterial Prostheses, Biomaterials 10 (1989) Apr. No. 3, pp. 156–165.

Molecular Biology of The Cell, Third Edition, 1994, Chapter 19: Cell Junctions, Cell Adhesion, and the Extracellular Matrix, pp. 963–1000.

*Primary Examiner*—David J. Isabella
(74) *Attorney, Agent, or Firm*—Hoffmann & Baron, LLP

(57) ABSTRACT

There is described a bio-compatible aqueous slurry for forming a fluid-tight barrier on a surface of a porous implantable article. This aqueous slurry includes a self-aggregating protein comminutate having a substantially uniform particle size, a bio-compatible plasticizer and water. This aqueous slurry is further characterized by having a viscosity of about 8,000 centipoise to about 60,000 centipoise at 25° C. and a pH sufficient to maintain the protein suspended in the slurry.

21 Claims, No Drawings

SELF-AGGREGATING PROTEIN COMPOSITIONS AND USE AS SEALANTS

This application is a divisional of copending application Ser. No. 08/814,533 filed on Mar. 10, 1997, now U.S. Pat. No. 6,177,609.

FIELD OF INVENTION

The present invention relates to improved bio-compatible fluid-tight barriers and barrier compositions for implantable articles. More particularly, this invention relates to highly controllable, bio-compatible aqueous slurry compositions and to processes for forming fluid-tight barriers when these compositions are coated onto or impregnated into an implantable prosthesis, such as a vascular graft or endoprosthesis.

BACKGROUND OF INVENTION

The use of implantable articles, such as porous synthetic vascular grafts, is a well accepted practice in the art. To improve certain properties of an implantable article, it is known to coat one or more surfaces of such articles with bio-compatible compositions. These coating compositions serve many different functions. For example, such coatings may render porous implantable articles blood-tight. In particular, U.S. Pat. No. 4,842,575 to Hoffman, Jr. et al. describes a process for rendering a synthetic vascular graft blood-tight by massaging a collagen preparation into the porous structure of the graft.

Alternatively, such coatings may be used to deliver certain pharmaceutical agents to targeted areas on an implantable article. For example, U.S. Pat. No. 5,290,271 to Jernberg describes encapsulated chemotherapeutics dispersed within a fluid or gel which are applied to a surface of an implant. In this way, the chemotherapeutic agents are released overtime to targeted areas on the implant.

Moreover, it is well known in the art to combine antibiotics, anti-thrombogenic agents and the like into coating and/or impregnating compositions that are applied to implantable articles. Such coatings increase the bio-compatibility of the implantable article by, for example, decreasing the risk of infection and blood clot formation thereon.

Coating and impregnation compositions for implantable articles like those described hereinabove can be made from a variety of materials. Such materials include, for example, biological molecule-containing compositions, polymer-containing compositions and hybrid polymer-biological molecule-containing compositions. For example, coating compositions known in the art for implantable articles include segmented linear polymers (U.S. Pat. No. 3,804,812 to Koroscil), heparinized polyurethane (U.S. Pat. No. 3,766,104 to Bonin et al.) and block copolymers of polysiloxane and polyurethane (U.S. Pat. No. 3,562,352 to Nyilas). Such compositions, however, may contain unreacted finctional groups which participate in undesirable side reactions in vivo and can inhibit cell ingrowth into, for example, a vascular graft. Such complications can lead to thrombus formation, infection, etc. at the implantation site.

Biological molecule-containing coatings include, for example, such extracellular matrix proteins as collagen, fibronectin, laminin and hyaluronic acid. The use of a slurry composition containing collagen to reduce the porosity of porous textile grafts is described in U.S. Pat. Nos. 4,842,575 and 5,108,424 to Hoffman et al. both of which are hereby incorporated by reference. During the processing of such prior art slurries, collagen of appropriate size and purity was obtained from previously processed calf skins that were passed through a meat grinder and extruded through a series of filter sieves of constantly decreasing mesh size. A plasticizer was then added to the collagen slurry and the composition was applied to, e.g., the surface of a porous vascular graft. The composition was then cross-linked and dried. The use of such slurries provides an implantable article, such as a vascular graft, with acceptable bio-compatibility and blood-tightness.

Room temperature grinding of, for example, bovine hides as a step in providing an aqueous dispersion of collagen is also described in U.S. Pat. No. 4,097,234 to Sohde et al. This patent, however, also teaches that when the pH of, for example, a preparation of bovine hides or tendons is in the range where the collagen to be isolated is easily solubilized or "swelled," the collagen fibers can become nonuniform and degraded due to the heat of friction caused from violent stirring or mechanical crushing of the preparation. Thus, Sohde et al. describe mincing bovine corium and then milling it in two successive steps at about room temperature, i.e., between 20° C.–25° C. The resultant aqueous dispersion is claimed to have collagen fibers of 4–12 $\mu$m in diameter, 2–25 mm in length and a viscosity of between ⅕ to ¹⁄₂₀ that of similar prior art compositions. The end products of the Sohde et al. method include non-woven fabric, films, membranes, tubes or sheets for use as artificial blood vessels, and sutures.

The method described by Sohde et al., however, suffers from the drawback that the grinding of the bovine tendons or hides is carried out at room temperature. Grinding of these tissues at room temperature raises the temperature of the micro-environment at the grinding site and causes the collagen to denature. This produces collagen having a higher solubility both in the medium in which it is produced and in the blood stream. Such higher solubility leads to premature absorption of the coating and can cause a deleterious affect on tissue ingrowth dynamics. Thus, the healing characteristics of the device are substantially hindered. Collagen derived from such a process is clearly not desirable as a sealant for an implantable article, such as for example, a porous vascular graft due to the risk of uneven or non-uniform distribution of the collagen particles within the sealant composition. Furthermore, the premature absorption of the collagen coating can result in undesirable leakage of blood from, e.g., a sealant coated porous vascular graft.

As an alternate method for preparing implantable collagen, several references describe cryogenic grinding of collagen. For example, U.S. Pat. No. 5,256,140 to Fallick describes a method for preparing an autologous source of injectable collagen for use in leveling skin having depressions therein. In this method, the skin of a patient who is to receive the collagen composition is made brittle by cooling it to between −10° F. to −100° F. (−3.8° C. to −37.8° C.) using, for example, liquid nitrogen. The brittle skin is then crushed using a mortar and pestle or cryogenically ground using a freezer mill. This preparation is then denatured and extracted in a weak acid solution so as to obtain denatured collagen for delivery into a patient.

Similarly, U.S. Pat. No. 5,332,802 to Kelman et al. describes auto-implantable collagen for use in plastic and ophthalmic surgery. In particular, to obtain the desired collagen preparation, a sample of a patient's skin is blended or homogenized by pulverizing the skin in a frozen state, such as by freezing the skin in liquid nitrogen and grinding the frozen skin using a mortar and pestle or by way of a cryopulverization mill. Such a treatment is used to increase the solubility of the contaminates therein and to reduce the overall processing time of the preparation.

Such cryogenic methods, however, are directed to cosmetic surgery-type applications and are unsuitable for sealant compositions used in conjunction with porous implantable articles. In particular, such methods are directed to the small-scale preparation of injectable collagen. Moreover, these compositions and methods are insufficient to produce non-denatured, uniform sized collagen preparations having highly controlled viscosity ranges.

As previously stated, collagen has been widely used as a coating and impregnating composition. In particular, its use as a fluid-tight barrier for textile prostheses, such as vascular and endovascular grafts has been very successful. Processing of collagen, however, has many difficulties, due to its inherent properties. For example, to make a reproducible collagen slurry requires certain consistencies in the raw material itself, as well as, the process steps and parameters. Naturally occurring materials such as collagen, will of course have many inherent variations. In order to produce acceptable sealant compositions, these variations must be minimized. One way to do so is through controlled sourcing and processing conditions. Notwithstanding such efforts to produce reliable and consistent compositions which are able to form reproducible sealants for porous substrates, such as vascular grafts, other difficulties are present which tend to compromise the quality and/or reproducibility of such sealants. For example, it is well known that collagen denatures above a certain temperature, e.g. 37° C. Once denaturization occurs, there is a loss in its natural self-aggregating properties. As a result, cross-linking is preferred or required. Additionally, grinding of raw collagen to specific particle sizes causes localized heating above its denaturization temperature. Such denaturization may go unnoticed in the early processing stages and end up in the final product. Thus, conventional grinding methods have limited usefulness due to the exposure of, e.g., collagen, to excessive heat build-up caused by the frictional grinding forces.

The prior art has also taught that cross-linking of the collagen was an important step in forming an effective sealant composition. See, for example, U.S. Pat. Nos. 4,842,575 and 5,108,424 to Hoffman et al. described hereinabove. It has recently been discovered in the course of the present invention that by eliminating the potential for denaturization and by controlling particle size, collagen compositions can be made which, under specified viscosity ranges, form reproducible, high quality sealants. The specified particle size is obtained without the concern for denaturization due to the use of cryogenic techniques as applied to the comminution process. The homogeneous particle size promotes uniformity in coating, further enhances the self-aggregating properties of the collagen and promotes the formation of a fluid-tight barrier. As a result of the present inventive processes, effective, high quality fluid-tight barriers can be obtained without cross-linking of the collagen.

In summary, all of the above-cited references generally suffer from an inability to produce highly controllable and reproducible collagen compositions. Thus, there is a need for improved bio-compatible aqueous slurry compositions and processes for forming fluid-tight barriers on implantable articles. In particular, there is a need for improved collagen compositions which contain non-denatured collagen having a uniform particle size and which have highly controllable and reproducible viscosities. The present invention is directed to meeting these and other needs.

SUMMARY OF INVENTION

The present invention relates to a bio-compatible aqueous slurry composition for forming a fluid-tight barrier on a surface of an implantable article. This slurry composition includes a self-aggregating protein comminutate having a substantially uniform particle size, a bio-compatible plasticizer and water. The slurry composition also has a viscosity of about 8,000 centipoise to about 60,000 centipoise at 25° C. and a pH sufficient to maintain the protein comminutate suspended therewithin.

In another embodiment of the present invention, there is described an implantable member for use in a body. This implantable member includes a flexible, porous polymeric substrate and an aqueous sealant composition in intimate contact with the porous substrate. The sealant composition includes a slurry which contains a self-aggregating protein comminutate having a uniform particle size, a bio-compatible plasticizer and water. This sealant composition is further characterized by having a viscosity of about 8,000 centipoise to about 60,000 centipoise at 25° C. and a pH sufficient to maintain the protein comminutate suspended within the slurry.

In yet another embodiment of the present invention, there is described a process for making a bio-compatible aqueous sealant slurry for rendering implantable articles fluid-tight. This process includes the steps of (1) providing a paste containing a bio-degradable self-aggregating protein, (2) milling the paste at cryogenic temperatures to a powder having a uniform particle size, (3) mixing the powder with a plasticizer and water to form the above-referenced aqueous sealant slurry which has a viscosity of about 8,000 centipoise to about 60,000 centipoise at 25° C. and (4) maintaining the slurry at a pH sufficiently outside of the isoelectric point of the paste to maintain the protein suspended within the slurry.

In a further embodiment of the present invention there is provided a process for preparing a fluid-tight implantable article. This process includes the steps of (1) providing an aqueous slurry containing a self-aggregating protein comminutate of uniform particle size, a bio-compatible plasticizer and water, wherein the slurry has a viscosity of about 8,000 centipoise to about 60,000 centipoise and a pH sufficient to maintain the protein comminutate suspended therewithin, (2) applying the slurry to a surface of a porous, flexible polymeric substrate with a force sufficient to ensure close association of the protein with the porous structure of the substrate, thereby sealing the article and (3) drying the slurry onto the substrate surface.

DETAILED DESCRIPTION OF THE INVENTION

While this invention is satisfied by embodiments in many different forms, there will be described herein in detail preferred embodiments of the invention with the understanding that the present disclosure is to be considered as exemplary of the principles of the invention and is not intended to limit the invention to the embodiments illustrated and described.

In accordance with the present invention, novel fluid-tight barrier compositions are provided. More particularly, novel compositions and processes are provided for the manufacture of collagen sealant compositions for rendering porous implantable substrates blood-tight.

In one embodiment of the present invention, there is provided a bio-compatible aqueous slurry for forming a fluid-tight barrier on a surface of a porous implantable article. For purposes of the present invention, "aqueous slurry" is intended to mean a water-based composition which is sufficiently fluid to flow and contains a mixture of finely divided particles including one or more self-aggregating proteins. This aqueous slurry forms fluid-tight barriers when brought into contact with a surface of an implantable article.

For purposes of the present invention, "porous implantable article" includes any bio-compatible article or substrate surface thereof to be implanted within a body, and particularly refers to porous tubular prostheses. Preferably, the implantable article is a polymeric vascular prostheses, such as a knitted or woven polyethylene terephthalate (PET), polytetrafluoroethylene (PTFE) or polyurethane vascular graft or endovascular graft. These articles may be fabricated using known manufacturing techniques and materials. The vascular grafts of the present invention may be made from biologically compatible fibers or yarns, such as for example, polyethylene terephthalate, commonly sold under the trademark DACRON and PTFE, or they may be made by known extrusion and expansion techniques such as those used in manufacturing PTFE and polyurethane grafts. Dipping shaped mandrels in various polymers, such as polyurethane, are also useful. Furthermore, the grafts may be knitted or woven and may be of a monofilament or a multi-filament yarn. The term "vascular prostheses" will be used herein to include all graft types, as well as, endoprosthesis, graft/stent and endovascular/stent combinations, mesh and hernia plugs and patches.

The bio-compatible slurry of the present invention includes a self-aggregating protein comminutate having a substantially uniform particle size, a bio-compatible plasticizer and water. For purposes of the present invention, the term "self-aggregating protein" is meant to encompass any protein which, when in an aqueous solution, is able to self-associate. Such proteins are also selected based on their ability to be absorbed by the body over time, to encourage healing and to promote tissue ingrowth into the implantable articles of the present invention. Suitable self-aggregating proteins include, without limitation, many members of the extracellular matrix family of proteins, such as collagen, fibronectin, vitronectin, proteoglycan, laminin, hyaluronic acid, tenascin, integrin cadherin, and mixtures thereof. These self-aggregating proteins may be obtained from any suitable mammalian species.

Preferably, the self-aggregating protein of the present invention belongs to the collagen family of extracellular matrix molecules which currently contains about 15 members. In addition to being self-aggregating, collagens are also capable of self-assembly from procollagen molecules to collagen molecules to collagen fibrils. Useful types of collagens include collagen types I through XV. See e.g., Bruce Alberts, Dennis Bray, Julian Lewis, Martin Raff, Keith Roberts and James D. Watson *Molecular Biology of the Cell*, 3rd ed. pgs. 963–1,000 (1994) which are hereby incorporated by reference. Preferably, the self-aggregating protein of the present invention is bovine type I collagen.

For purposes of the present invention, the self-aggregating protein may be present in the slurry composition at a concentration which allows the slurry to be easily and uniformly applied to an implantable article and which is sufficient to cause a fluid-tight barrier to form thereon. Preferably, the self-aggregating protein is present in the slurry composition at a concentration of from about 1% to about 3% by weight. More preferably, the self-aggregating protein is present in the slurry composition at a concentration of about 1.1% to about 2.0% by weight.

By "comminutate" it is meant that the self-aggregating protein is reduced to a powder of substantially uniform size by, for example, attrition, impact, crushing, grinding, abrasion, milling, chemical methods and combinations thereof followed by or including screening or sieving through the desired mesh size. Other techniques capable of producing particulates are also contemplated. Prior to comminutation, the self-aggregating protein is cryogenically processed to form a solid from the aqueous paste. The solid is then comminuted to the desired particle size. Frictional forces which contribute to localized heat build-up and denaturization do not deleteriously affect the cryogenically solidified mass. Thus, the particle size of the self-aggregating protein can be controlled without concern for loss of its inherent self-aggregating properties which normally occur to proteins, such as collagen, when denatured. This is an important feature, because the smaller particle sizes required in the present invention may require rigorous comminution which would otherwise lead to denaturization.

Preferably, the self-aggregating protein is reduced to a uniform particle size by a cryogenic milling process. As discussed in more detail hereinbelow, this cryogenic milling process is accomplished by taking a raw paste containing the self-aggregating protein and extruding it through, for example a meat grinder to obtain a more convenient and workable size, freezing the extruded material at cryogenic temperatures, maintaining such material at cryogenic temperatures while grinding the material to a powder, passing the powder through a sieve and collecting the uniformly sized particles therefrom. The passage through a meat-grinder or similar machine does not generate sufficient heat to affect the protein structure. For purposes of the present invention, cryogenic freezing means an almost instantaneous freezing by immersion in liquid nitrogen. Other suitable freezing techniques as known in the art are also contemplated so long as the self-aggregating protein is maintained at a temperature below its denaturization point during comminution to the desired particle size.

By use of the cryogenic milling process of the present invention, a frozen self-aggregating protein paste is reduced to a powder of uniform particle size without risk of denaturing the protein. In particular, because the protein is continuously maintained at cryogenic temperatures throughout the milling process, there is no risk that it will be subjected to denaturing temperatures, i.e., temperatures in excess of 37° C., even at the localized milling surfaces. Thus, subsequent sealant compositions formed from a protein processed in this manner are easily controllable, comprise particles which are highly uniform in diameter, and possess barrier properties which are readily reproducible.

For purposes of the present invention, "uniform particle size" means that the cryogenically milled and sieved particles derived from the self-aggregating protein have substantially the same diameter. Furthermore, the screen sizes for sieving the present cryogenically milled self-aggregating proteins are in the range from about 0.020 inches to about 0.062 inches (0.5 mm–1.55 mm). A single screen size is generally chosen for a particular coating composition such that uniformity in particle size exists in the final coating. This range of screen sizes produces self-aggregating protein particles having diameters of about 5 $\mu$m to about 750 $\mu$m, depending upon the chosen screen size.

The size of the particles used in the present invention is one factor used to control the viscosity of the final slurry composition. Not wishing to be bound by a particular theory, it is believed that these non-denatured small, uniformly sized particles are critical to the operation of the present invention. In particular, it is believed that the above-referenced properties of these particles enable them to combine faster and to form stronger, more cohesive sealant compositions, without cross-linking, than previous prior art compositions. Thus, cryogenic milling of the self-aggregating protein followed by sieving of the protein comminutate provides the skilled artisan with an unprecedented level of control over the physical properties of the final slurry composition, including viscosity, protein dispersion and reproducibility. Such control is vital for producing vascular prostheses, such as grafts and endografts, having safe, reliable and consistent barrier properties.

As set forth hereinabove, the viscosity of the aqueous slurry must be carefully controlled. In particular, the viscosity of the aqueous slurry must be such that sufficient self-aggregating particles are present to form an effective barrier coating or impregnation to prevent unwanted leakage of, for example, blood, through a porous vascular prosthesis treated therewith. At the same time, however, the aqueous slurry must have enough flow so that it is easily applied to a porous substrate. Accordingly, viscosities which meet these general limitations may be used in the present invention. Preferably, the aqueous slurry composition containing the self-aggregating protein has a viscosity of between about 8,000 centipoise (cps) to about 60,000 cps at 25° C. More preferably, the aqueous slurry composition has a viscosity of between about 30,000 cps to about 50,000 cps at 25° C. As discussed previously, the particle size of the protein in the aqueous slurry influences its viscosity.

Additional parameters, however, are also used to control the viscosity of the slurry composition. For example, the temperature and pH of the slurry composition, the amount of mixing the slurry composition is subjected to and the final concentration of the self-aggregating protein in the final slurry composition are additional factors influencing the final viscosity thereof. The pH of the aqueous slurry must be monitored in order to ensure that it remains in an aqueous state. It is within the knowledge of the skilled artisan to select an appropriate pH based on the isoelectric point of the raw material, e.g., based on the isoelectric point of the self-aggregating protein contained therein. For example, the pH of the slurry should be maintained no less than 0.3 pH units away from the isoelectric point of the raw material. In the case of limed bovine skin type I collagen in which the isoelectric point is 4.2, it is preferred that the pH of the aqueous slurry be maintained in the range of about 3.5 to about 3.9.

As stated hereinabove, the aqueous slurry composition of the present invention also contains a biologically acceptable plasticizer for enhancing the flexibility and handling characteristics of the implantable article. Suitable plasticizers include polyhydric alcohols including for example, glycerol, sorbitol and mannitol. Preferably, the plasticizer accounts for between about 8% to about 30% by weight of the aqueous slurry.

Additionally, optional agents may also be added to the present aqueous slurry composition. These agents may be used for the purposes of bioburden control, or to modify the flow characteristics of the slurry. The use of such agents can lead to a device with lower permeabilities. Accordingly, such agents will be referred to hereinafter as "permeability lowering compositions." An example of such an agent is ethanol. Moreover, when reagents like ethanol are used, they confer the added benefit of functioning as bacteriostatic agents. Preferably, the permeability lowering composition, if used, accounts for up to about 24% by weight of the aqueous slurry composition.

Bio-active agents may also be added to the present aqueous slurry composition. Such agents may be added to the slurry composition to reduce the risk of infection or thrombus formation associated with the implantation of an implantable article of the present invention. Suitable bio-active agents include, for example, antibiotics, anticoagulants, antibacterial agents and mixtures thereof.

As set forth hereinabove, the aqueous slurry composition of the present invention renders the implantable article fluid-tight. For purposes of the present invention, "fluid-tight" is intended to mean that the porous implantable article is rendered essentially non-permeable to liquids, such as for example, blood.

To achieve the desired level of fluid-tightness, the aqueous slurry composition of the present invention is placed in intimate contact with a porous implantable article. In the case of a vascular graft, the aqueous slurry composition is placed in intimate contact therewith by coating or impregnating methods. Such methods include placing the aqueous slurry composition within the graft and forcing it through the pores of the graft with sufficient force to cause the slurry composition to either coat the surface or penetrate into the pores and interstices of the graft. The force used to distribute the slurry composition through the porous article may be supplied by pressure means, such as mechanical rollers and the like, or fluidized pressure.

Multiple applications of the present aqueous slurry composition may be applied to the implantable article. Preferably, between three (3) to six (6) applications of the aqueous slurry composition are applied to the implantable article. Between each application of the aqueous slurry composition, the slurry coated implant is dried. This drying is accomplished in an oven having a temperature between about 25° C. to about 35° C. for about 45–75 minutes.

While it is an advantage of the present invention over the prior art that cross-liking is not required to form an effective fluid barrier, a cross-linking agent may also be optionally added to the aqueous slurry composition, if desired. In such cases, the self-aggregating proteins in the slurry composition are cross-linked prior to drying of, e.g., the slurry coated vascular graft. Any bio-compatible cross-linking agent may be used to cross-link the self-aggregating proteins of the present invention. Suitable cross-linking agents include, for example, formaldehyde and glutaraldehyde. Preferably, the cross-linking agent is present in the aqueous slurry composition from about 0 to about 500 parts per million. Alternatively, the cross-linking agent may be introduced following application of the slurry in either solution or gaseous form.

In another embodiment of the present invention, there is provided an implantable member for use in a body. This implantable member includes a flexible, porous polymeric substrate as previously described. An aqueous sealant composition is in intimate contact with the porous substrate. This sealant composition includes a slurry of a self-aggregating protein comminutate, a bio-compatible plasticizer and water. Each of the components of this slurry are separately described hereinabove. Furthermore, as set forth above, the viscosity of the sealant composition is maintained between about 8,000 cps and about 60,000 cps. Moreover, the pH of the sealant composition is controlled in order to maintain the protein in suspension in the slurry.

In a preferred embodiment, a porous vascular graft, as hereinbefore described, is coated and/or impregnated with the inventive sealant composition to form a fluid-tight barrier thereon.

In a further embodiment of the present invention, there is disclosed a process for making a bio-compatible aqueous sealant slurry for rendering implantable articles fluid-tight. As set forth in more detail below, this process includes the steps of (1) providing a paste containing a bio-absorbable self-aggregating protein, (2) milling the paste at cryogenic temperatures to a powder having a uniform particle size, (3) mixing the powder with a plasticizer and water to form the above-referenced aqueous sealant slurry which has a viscosity of about 8,000 centipoise to about 60,000 centipoise at 25° C. and (4) maintaining the slurry at a pH sufficiently outside of the isoelectric point of the paste to maintain the self-aggregating protein dispersed in the slurry.

In yet another embodiment of the present invention, there is provided a process for preparing a fluid-tight implantable article. This process includes the steps of (1) providing an aqueous slurry as described hereinabove, (2) applying the slurry to a surface of a porous, flexible polymeric substrate with a force sufficient to ensure close association of the protein with the porous structure of the substrate, and (3) allowing the slurry to dry.

The following examples are set forth to illustrate the process of preparing the slurry and fluid-tight implantable articles of the present invention. These examples are provided for purpose of illustration only and are not intended to be limiting in any sense.

EXAMPLE 1

Preparation of Self Aggregating Protein Paste

Self aggregating proteins in accordance with the present invention are prepared from the appropriate source, including cell and organ cultures, as well as whole organ explants. In the case of collagen type I and III, fresh calf skins are mechanically stripped from the carcasses of young calves, fetuses or stillborns and washed in a rotating vessel with cold running water until the water is observed to be free from surface dirt, blood and/or tissues. The subcutis is mechanically cleaned to remove contaminating tissues, such as fat and blood vessels. Subsequently, the skins are cut in the longitudinal direction into strips about 12 cm wide and are placed in a wood or plastic vessel as commonly used in the leather industry.

The skins are dehaired with a flusher solution of 1M $Ca(OH)_2$ for 25 hours. Alternatively, the skins may be dehaired by mechanical means or by a combination of chemical and mechanical means. Following dehairing, the skins are cut into pieces of approximately 1"×1" and are washed in cold water.

Following washing, 120 kg of the bovine skins are placed in a vessel containing 260 L water, 2 L NaOH (50%) and 0.4 L $H_2O_2$ (35%). These components are mixed slowly for 12 to 15 hours at 4° C. and are washed with an excess of tap water for 30 minutes to provide partially purified skins. These skins are limed in a solution of 260 L water, 1.2 L NaOH (50%) and 1.4 kg $CaCO_3$ for 5 minutes with slow mixing. This treatment is continued twice a day for 25 days. Preferably, this liming process continues as described for 0–8 days. Following this treatment, the solution is decanted and discarded. The skins are then washed with an excess of tap water for 90 minutes under constant stirring.

The skins are acidified in a solution containing 14 kg HCL (35%) in 70 L water with vigorous stirring. The acid is allowed to penetrate into the skins for about 6 hours. Following acidification, the skins are washed in an excess of tap water for about 4 hours or until a pH of about 5 is reached. The pH of the skins is then readjusted to 3.3 to 3.4 using acetic acid containing 0.5% of a preservative. The purified skins are then made into a raw paste by grinding in a meat grinder and extruding the ground skins under pressure through a series of filter sieves of constantly decreasing mesh size. The final product is a white homogenous smooth paste of pure bovine skin-derived type I collagen. This raw collagen paste is stored at 0–25° C. until further use.

EXAMPLE 2

Cryogenic Milling Process

Optionally, to accommodate the size of certain milling machinery, 25 kg of the raw paste of Example 1 is made into processable-sized curds by extruding the raw paste through a meat grinder. The meat grinder is outfitted with an extrusion plate having holes through which the raw paste is extruded. Preferably, the holes are between about ⅛" to about ⅜" in diameter.

As the raw paste is extruded, it is allowed to fall into a cryogenic bath containing, for example, liquid nitrogen. When the extrudate hits the cryogenic bath, it immediately freezes and takes on a curd-like shape. These curds are then milled to a powder-like consistency at cryogenic temperatures in, for example, a SPEX 6700 Freezer/Mill (Spex Industries, Inc.; Edison, N.J.).

This cryogenically milled powder is passed through a sieve and the sieved material collected. The diameter of each particle in this sieved material is highly uniform. Mesh or screen sizes of the sieving screen can vary between about 0.020 inches to about 0.062 inches (0.5 mm–1.55 mm). Such a range in screen size produces uniform particles having a diameter of about 5 $\mu$m to about 750 $\mu$m, depending upon which screen is used. This powder is preferably stored at temperatures below 0° C. to prevent agglomeration.

EXAMPLE 3

Slurry Preparation and Graft Formation

An aqueous slurry of a bovine type I collagen is prepared according to Example 2 using 1.6% by weight of the collagen powder, 8–30% by weight of glycerin with the balance being water. The viscosity of this slurry is measured at 25° C. Only collagen slurry preparations having a viscosity of between about 8,000 cps and about 60,000 cps are retained for further processing. Preferably, the viscosity range of the slurry is between about 30,000 cps and about 50,000 cps. Aqueous slurry meeting this viscosity criteria is then applied to a porous vascular graft under pressure of about 15 psi. This pressure forces the slurry into intimate contact with the internal porous structure of the graft. The graft is then dried in an oven at about 25° C. to about 35° C. for between about 45 to about 75 minutes. Multiple applications of the slurry may be made to the graft. Preferably between 3 to 6 applications of the slurry are made to the graft followed by a drying cycle as described herein between each application. The final graft is then sterilized using gamma radiation.

Optionally, 0–24% of ethanol is added to the slurry to lower the permeability of the final graft. The collagen particles in the slurry are also optionally cross-linked with 0–500 parts per million formaldehyde prior to application to the vascular graft. Bio-active agents are also optionally added to the collagen slurry. These bio-active agents include, for example, antibiotics, anticoagulants and anti-bacterial agents. Preferably, heparin is added to the slurry to increase the anti-thrombogenicity of the collagen slurry. Grafts made in this manner have essentially zero porosity, i.e., the grafts have a sufficiently low permeability that preclotting is not required prior to implantation.

EXAMPLE 4

Porosity Tests of Porous Vascular Grafts

The porosity of, e.g., a collagen treated fabric graft of the present invention is reduced to less than about 1% after three applications as follows. A standard water porosity test used to measure water porosity of a graft is as follows. A column of water equivalent to 120 mm Hg pressure is allowed to flow through a 0.5 cm$^2$ orifice having a sample of the graft over the orifice for one minute. The amount of water collected in 1 minute is measured and the porosity calculated and expressed as ml/min/cm$^2$, several readings are taken for each sample.

The water porosity of a non-treated Microvel graft fabric (Meadox Medicals, Inc., Franklin Lakes, N.J.) was about 1,900 ml/min/cm$^2$. The porosity after treating the graft with a composition of the present invention is as follows:

TABLE I

| Number of Coatings | Porosity |
|---|---|
| 0 | 1,900 |
| 1 | 266 |
| 2 | 146 |
| 3 | 14 |
| 4 | 5 |
| 5 | 2 |
| 6 | 0 |

In each case the collagen coating is a bovine skin derived-plasticized slurry prepared in accordance with the composition described in Example 3. Based on the results of Table I, it is preferable to provide a collagen impregnated graft treated with at least three applications of the present slurry compositions; and most preferable with four or five applications with drying between each application.

EXAMPLE 5

Preparation of Collagen Type II Slurry Composition

The slurry of Example 3 is made as described with the exception that collagen type II is substituted for collagen type I. The properties of the slurry coated graft are substantially identical to Example 3 in flexibility, handling and fluid tightness.

EXAMPLE 6

Preparation of Collagen Type III Slurry Composition

The slurry of Example 3 is made as described with the exception that collagen type III is substituted for collagen type I. The properties of the slurry coated graft are substantially identical to Example 3 in flexibility, handling and fluid tightness.

EXAMPLE 7

Preparation of Collagen Type IV Slurry Composition

The slurry of Example 3 is made as described with the exception that collagen type IV is substituted for collagen type I. The properties of the slurry coated graft are substantially identical to Example 3 in flexibility, handling and fluid tightness.

EXAMPLE 8

Preparation of Collagen Type V Slurry Composition

The slurry of Example 3 is made as described with the exception that collagen type V is substituted for collagen type I. The properties of the slurry coated graft are substantially identical to Example 3 in flexibility, handling and fluid tightness.

EXAMPLE 9

Preparation of Collagen Type VI Slurry Composition

The slurry of Example 3 is made as described with the exception that collagen type VI is substituted for collagen type I. The properties of the slurry coated graft are substantially identical to Example 3 in flexibility, handling and fluid tightness.

EXAMPLE 10

Preparation of Collagen Type VII Slurry Composition

The slurry of Example 3 is made as described with the exception that collagen type VII is substituted for collagen type I. The properties of the slurry coated graft are substantially identical to Example 3 in flexibility, handling and fluid-tightness.

EXAMPLE 11

Preparation of Collagen Type VIII Slurra Composition

The slurry of Example 3 is made as described with the exception that collagen type VIII is substituted for collagen type I. The properties of the slurry coated graft are substantially identical to Example 3 in flexibility, handling and fluid tightness.

EXAMPLE 12

Preparation of Collagen Type IX Slurry Composition

The slurry of Example 3 is made as described with the exception that collagen type IX is substituted for collagen type I. The properties of the slurry coated graft are substantially identical to Example 3 in flexibility, handling and fluid tightness.

EXAMPLE 13

Preparation of Collagen Type X Slurry Composition

The slurry of Example 3 is made as described with the exception that collagen type X is substituted for collagen type I. The properties of the slurry coated graft are substantially identical to Example 3 in flexibility, handling and fluid tightness.

EXAMPLE 14

Preparation of Collagen Type XI Slurry Composition

The slurry of Example 3 is made as described with the exception that collagen type XI is substituted for collagen type I. The properties of the slurry coated graft are substantially identical to Example 3 in flexibility, handling and fluid tightness.

EXAMPLE 15

Preparation of Collagen Type XII Slurry Composition

The slurry of Example 3 is made as described with the exception that collagen type XII is substituted for collagen type I. The properties of the collagen coated graft are substantially identical to Example 3 in flexibility, handling and fluid tightness.

EXAMPLE 16

Preparation of Collagen Type XIII Slurry Composition

The slurry of Example 3 is made as described with the exception that collagen type XIII is substituted for collagen type I. The properties of the slurry coated graft are substantially identical to Example 3 in flexibility, handling and fluid tightness.

EXAMPLE 17

Preparation of Collagen Type XIV Slurry Composition

The slurry of Example 3 is made as described with the exception that collagen type XIV is substituted for collagen type I. The properties of the slurry coated graft are substantially identical to Example 3 in flexibility, handling and fluid tightness.

EXAMPLE 18

Preparation of Collagen Type XV Slurry Composition

The slurry of Example 3 is made as described with the exception that collagen type XV is substituted for collagen type I. The properties of the slurry coated graft are substantially identical to Example 3 in flexibility, handling and fluid tightness.

EXAMPLE 19

Preparation of Fibronectin Slurry Composition

The slurry of Example 3 is made as described with the exception that fibronectin is substituted for collagen type I. The properties of the slurry coated graft are substantially identical to Example 3 in flexibility, handling and fluid tightness.

EXAMPLE 20

Preparation of Vitronectin Slurry Composition

The slurry of Example 3 is made as described with the exception that vitronectin is substituted for collagen type I. The properties of the slurry coated graft are substantially identical to Example 3 in flexibility, handling and fluid tightness.

EXAMPLE 21

Preparation of Proteoglycan Slurry Composition

The slurry of Example 3 is made as described with the exception that a proteoglycan is substituted for collagen type I. The properties of the slurry coated graft are substantially identical to Example 3 in flexibility, handling and fluid tightness.

EXAMPLE 22

Preparation of Laminin Slurry Composition

The slurry of Example 3 is made as described with the exception that laminin is substituted for collagen type I. The properties of the slurry coated graft are substantially identical to Example 3 in flexibility, handling and fluid tightness.

EXAMPLE 23

Preparation of Hyaluronic Acid Slurry Composition

The slurry of Example 3 is made as described with the exception that hyaluronic acid is substituted for collagen type I. The properties of the slurry coated graft are substantially identical to Example 3 in flexibility, handling and fluid tightness.

EXAMPLE 24

Preparation of Tenascin Slurry Composition

The slurry of Example 3 is made as described with the exception that tenascin is substituted for collagen type I. The properties of the slurry coated graft are substantially identical to Example 3 in flexibility, handling and fluid tightness.

EXAMPLE 25

Preparation of Integrin Slurry Composition

The slurry of Example 3 is made as described with the exception that an integrin is substituted for collagen type I. The properties of the slurry coated graft are substantially identical to Example 3 in flexibility, handling and fluid tightness.

EXAMPLE 26

Preparation of Cadherin Slurry Composition

The slurry of Example 3 is made as described with the exception that a cadherin is substituted for collagen type I. The properties of the slurry coated graft are substantially identical to Example 3 in flexibility, handling and fluid tightness.

EXAMPLE 27

In a triangle test, experts in the field where asked to compare the physical properties of a prior art graft and a graft of the present invention. The expert respondents used in this study consisted of 47 Thoracic Surgeons (all users of a prior art collagen coated vascular graft) in attendance at the STS Convention in Palm Springs, Calif., Jan. 29–Feb 1, 1995. Woven 30 mm vascular grafts were used in this test.

The triangle test included presenting three samples of vascular grafts either simultaneously or successively to each respondent. Two of the grafts presented to each respondent were always coated with the same composition; the third graft was always coated with a different composition. Each respondent was required to pick the sample believed to be different. After successfully selecting the different sample, the respondent was asked which of the two types of grafts they preferred.

In order to neutralize order and presentation bias, both grafts coated with a prior art composition and grafts coated with the present compositions were used equally often as the different sample (i.e., half of the respondents were given to evaluate two grafts coated with the present composition and one prior art sample and half were given to evaluate two prior art samples and one sample according to the present invention). In addition, all samples were presented an equal number of times in 1st, 2nd and 3rd positions.

After meeting the above-referenced screening requirements, each respondent was given three samples to evaluate for handling characteristics. Respondents were instructed to cut and suture the samples and to identify which was the different sample. After making their selection, they were then asked to select the preferred sample(s) and provide a reason for their preference. Only those respondents that correctly identified the different sample were included in the preference analysis.

The results of the triangle study and preference analysis indicated that 80% of the experts were able to distinguish between a vascular graft coated with a prior art composition and a vascular graft coated with a composition of the present invention. Furthermore, 87% of the experts who were able to distinguish between the two samples preferred the graft coated with a composition of the present invention. The following characteristics were cited by the experts as reasons for choosing the graft coated with composition of the present invention: superior softness (71%); superior flexibility (56%), superior suturability (38%).

By way of summary, as the triangle test and preference analysis demonstrate, the compositions of the present invention allow for more repeatable and uniform properties in the final graft product, including better handling properties, i.e., a more consistently obtained soft-feel and flexibility. This is in contrast to prior art methods which did not use a controlled particle size in the present range, and which resulted in a wider degree of variation in the final product including variation in the "hand".

The invention being thus described, it will be obvious that the same may be varied in many ways. Such variations are not to be regarded as a departure from the spirit and scope of the invention and, all such modifications are intended to be included within the scope of the following claims.

What is claimed is:

1. An implantable member for use in a body comprising:
   a flexible, porous polymeric substrate; and
   an aqueous sealant composition in intimate contact with said porous substrate, said sealant composition comprising:
      a slurry of a self-aggregating protein comminutate having a uniform particle size,
      a bio-compatible plasticizer,
      and water, wherein said sealant composition has a viscosity of about 8,000 centipoise to about 60,000 centipoise at 25° C. and a pH sufficient to maintain said protein comminutate suspended therewithin.

2. The implantable member of claim 1, wherein said self-aggregating protein is present in said sealant composition at concentrations of from about 1% to about 3% by weight.

3. The implantable member of claim 1, wherein said self-aggregating protein is selected from the group consisting of collagen, fibronectin, vitronectin, proteoglycan, laminin, hyaluronic acid, tenascin, integrin, cadherin and mixtures thereof.

4. The implantable member of claim 3, wherein said self-aggregating protein is type I bovine collagen.

5. The implantable member of claim 1, wherein said sealant composition further comprises a permeability lowering composition.

6. The implantable member of claim 5, wherein said permeability lowering composition further comprises up to about 24% ethanol.

7. The implantable member of claim 1, wherein said plasticizer is one of glycerol and sorbitol.

8. The implantable member of claim 7, wherein said plasticizer is present in said sealant composition at about 8% to about 30% by weight.

9. The implantable member of claim 1, wherein said aggregated protein is cross-linked.

10. The implantable member of claim 9, wherein said protein is cross-linked with one of formaldehyde and glutaraldehyde.

11. The implantable member of claim 1, wherein said sealant composition further comprises a bio-active agent.

12. The implantable member of claim 11, wherein said bio-active agent is selected from the group consisting of antibiotics, anticoagulants, antibacterial agents and mixtures thereof.

13. The implantable member of claim 11, wherein said viscosity is about 30,000 centipoise to about 50,000 centipoise.

14. The implantable member of claim 1, wherein said pH is from about 3.5 to about 3.9.

15. A process for preparing a fluid-tight implantable article comprising:
   a) providing an aqueous slurry containing a self-aggregating protein comminutate of uniform particle size, a bio-compatible plasticizer and water, said slurry also having a viscosity of about 8,000 centipoise to about 60,000 centipoise and a pH sufficient to maintain said protein suspended within said slurry;
   b) applying said slurry to a surface of a porous, flexible polymeric substrate with a force sufficient to ensure close association of said protein with said porous structure of said substrate, thereby sealing said article; and
   c) drying said slurry onto said substrate surface.

16. The process of claim 15, wherein said protein is cross-linked prior to said drying step.

17. The process of claim 15, wherein said uniform particle size is between about 5 μm to about 750 μm.

18. The process of claim 15, wherein said pH is between about 3.5–3.9.

19. The process of claim 15, wherein said sealant slurry has a viscosity of about 30,000 centipoise to about 50,000 centipoise.

20. The process of claim 15, wherein said force is pressure.

21. An implantable fluid-tight film for sealing a porous implantable article, said film formed by depositing and drying an aqueous slurry, said aqueous slurry comprising:
   (i) a self-aggregating protein comminutate powder having a substantially uniform particle size;
   (ii) a biocompatible plasticizer; and
   (iii) water;
      wherein said slurry (a) comprises a sufficient concentration of comminutate powder to provide said fluid tight film; (b) has a viscosity of about 8,000 to about 60,000 centipoise at 25° C.; and (c) a pH sufficient to maintain said comminutate powder suspended therein for forming said fluid-tight film.

* * * * *

UNITED STATES PATENT AND TRADEMARK OFFICE
CERTIFICATE OF CORRECTION

PATENT NO. : 6,299,639 B1
DATED : October 9, 2001
INVENTOR(S) : Castro et al.

It is certified that error appears in the above-identified patent and that said Letters Patent is hereby corrected as shown below:

Column 11,
Line 15, "...and expressed as ml/min/cm$^2$, several readings are taken for each sample." should read -- ...and expressed as ml/min/cm$^2$. Several readings are taken for each sample. --.

Column 12,
Line 35, "Preparation of Collagen Type VIII Slurra" should read -- Preparation of Collagen Type VIII Slurry --.

Signed and Sealed this

Ninth Day of April, 2002

Attest:

JAMES E. ROGAN
*Attesting Officer*  *Director of the United States Patent and Trademark Office*